US00PP28678P3

(12) United States Plant Patent
Suphachadiwong

(10) Patent No.: US PP28,678 P3
(45) Date of Patent: Nov. 21, 2017

(54) *VANDA* PLANT NAMED 'SPCDW1508'

(50) Latin Name: ***Vanda* Jones ex R. Br.**
Varietal Denomination: SPCDW1508

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 25 days.

(21) Appl. No.: 14/999,719

(22) Filed: Jun. 17, 2016

(65) Prior Publication Data

US 2016/0374251 P1 Dec. 22, 2016

(30) Foreign Application Priority Data

Jun. 19, 2015 (QZ) ..... PBR 2015/1388

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1508' which is characterized by sepals and petals with a white to light violet base color and a prominent dark violet irregular tessellation pattern, overlapping sepals and petals which twist in a propeller-like fashion, excellent plant vigor, and the stability of these characteristics from generation to generation.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1508'.

CROSS REFERENCE TO RELATED APPLICATIONS

This application claims priority to the Community Plant Variety Rights application number 2015/1388, filed Jun. 19, 2015, which is herein incorporated by reference.

BACKGROUND OF THE INVENTION

Parentage: The *Vanda* variety 'SPCDW1508' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in August of 1994.

The new variety was first selected in February of 2001, in a research greenhouse in Bangphra, Thailand belonging to the inventor. After identifying the new variety as a potentially interesting selection, the inventor continued confidential testing and propagation of 'SPCDW1508', assessing stability of the unique characteristics of this variety.

Asexual Reproduction: Asexual reproduction of the new cultivar 'SPCDW1508', by way of mericloning, was first initiated in July of 2007 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1508' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1508'. These characteristics in combination distinguish 'SPCDW1508' as a new and distinct *Vanda* cultivar:

1. *Vanda* 'SPCDW1508' exhibits sepals and petals with a white to light violet base color; and
2. *Vanda* 'SPCDW1508' exhibits sepals and petals with a prominent dark violet irregular tessellation pattern; and
3. *Vanda* 'SPCDW1508' exhibits overlapping sepals and petals which twist in a propeller-like fashion; and
4. *Vanda 'SPCDW*1508' exhibits excellent plant vigor.

BOTANICAL DESCRIPTION OF THE PLANT

Figure 1:
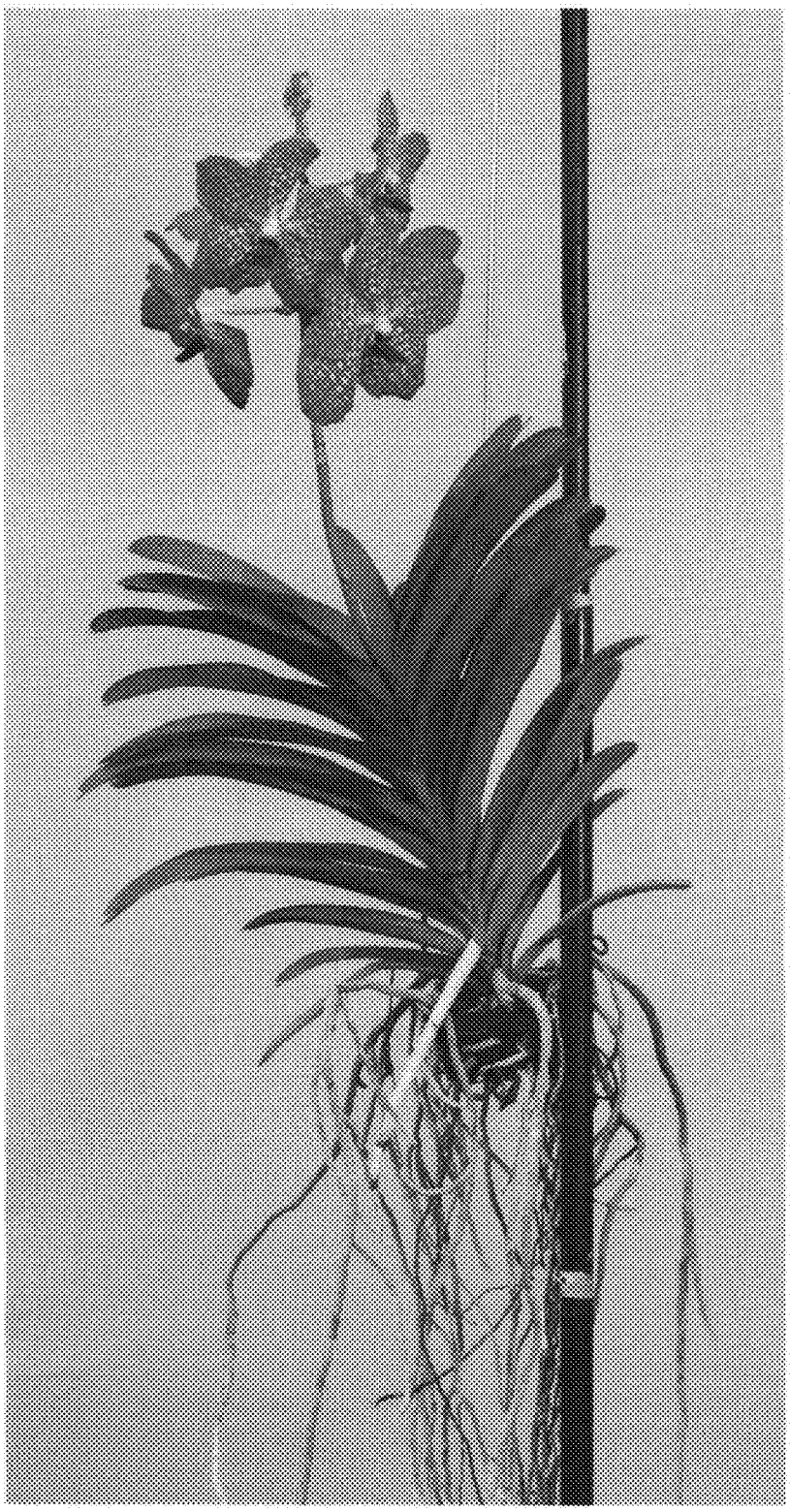
FIG. 1 illustrates, as nearly true as it is reasonably possible to make the same in color photographs of this type, an exemplary plant of 'SPCDW1508' grown in a commercial greenhouse in Honselersdijk, the Netherlands. This plant is approximately 6 years old from the time of mericloning, shown planted in an 8 by 8 cm container.
Figure 2:
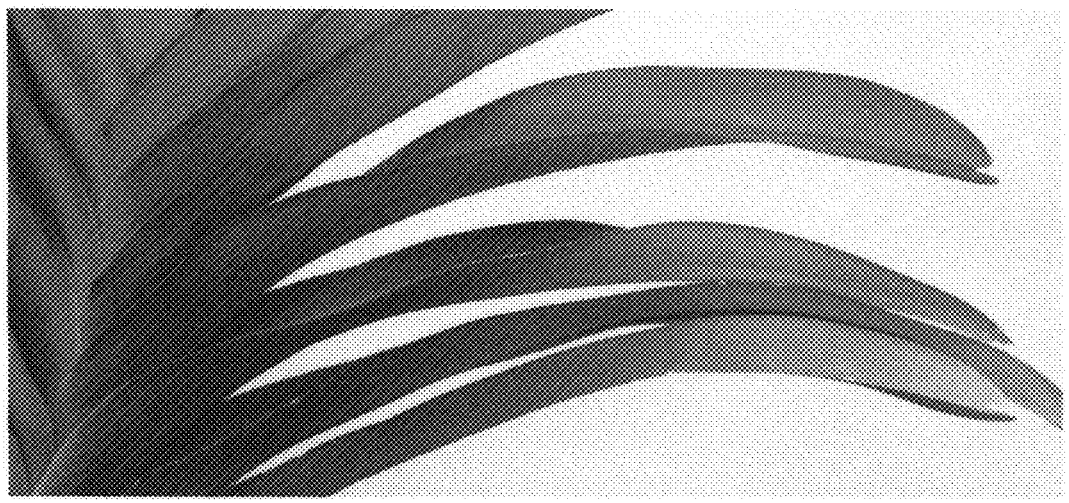
FIG. 2 illustrates, as nearly true as it is reasonably possible to make the same in color photographs of this type, the typical foliage of 'SPCDW1508'.
Figure 3:
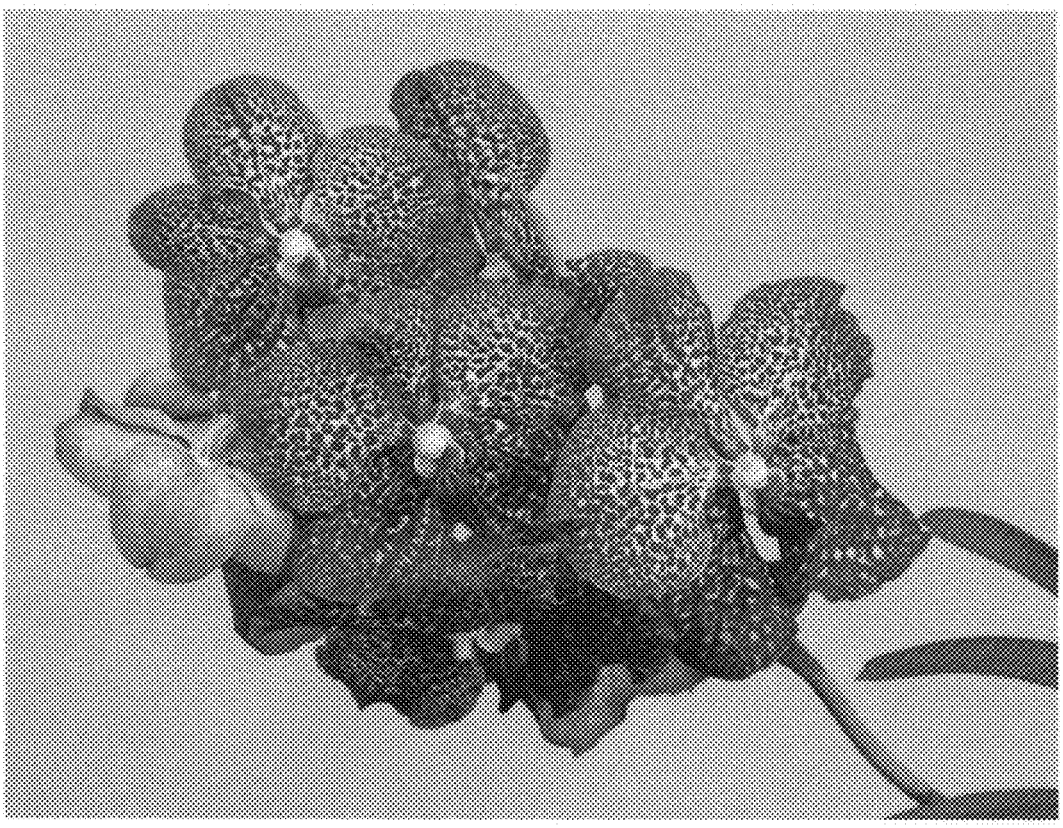
FIG. 3 illustrates, as nearly true as it is reasonably possible to make the same in color photographs of this type, the typical inflorescence and flower of 'SPCDW1508'.

The following observations and measurements made in April of 2016 describe averages from a sample set of six specimens of six year-old 'SPCDW1508' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1508' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1508' and comparisons with other varieties of *Vanda* are provided below.

Plant description:

- *Growth habit.*—Perennial; monopodial, upright. Single monopodial leafy stem, with flowers carried above the leaf plane, inflorescences grow from the leaf axils.
- *Average height from base (plant grown in hanging basket, so no soil line present) to foliar plane.*—34.5 cm.
- *Average height from base (plant grown in hanging basket, so no soil line present) to top of floral plane.*—56.7 cm.
- *Plant spread.*—Average of 33.7 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—57.2 cm long with a diameter of 0.5 cm, on average.
- *Texture.*—Very fleshy; non-fibrous.
- *Color.*—Greyed-Green, near RHS 192B to 192C; root apex is yellow-green, RHS 147B to 147C.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—18.4 cm.
- *Diameter.*—1.1 cm.
- *Internode length.*—1.2 cm.
- *Luster.*—Matte.
- *Aspect.*—Near vertical.
- *Strength.*—Very strong.
- *Color, juvenile.*—Yellow-green, near RHS 150D.
- *Color, mature.*—Yellow-green, near RHS 150D.
- *Color at internodes.*—Greyed-orange, near RHS164B to 164C.
- *Pubescence.*—Glabrous.

Foliage:

- *Arrangement.*—Distichous.
- *Quantity.*—Approximately 30 leaves per plant.
- *Dimensions.*—22.2 cm long and 3.1 cm wide, on average.
- *Shape of blade.*—Ligulate; moderately to strongly carinate.
- *Aspect.*—Slightly curved.
- *Apex.*—Unequal praemorse.
- *Base.*—Sheathing.
- *Sheath dimensions.*—3.2 cm long and 1.4 cm wide, on average.
- *Sheath color.*—Yellow-green, near RHS 150D.
- *Margin.*—Entire.
- *Pubescence, texture and luster of adaxial surface.*—Glabrous, smooth, and slightly glossy.
- *Pubescence, texture and luster of abaxial surface.*—Glabrous, smooth, and matte.
- *Color.*—Juvenile foliage, adaxial surface — Yellow-green, near RHS 144A, and green towards the margins, near RHS 143A. Juvenile foliage, abaxial surface — Green, near RHS 143A. Mature foliage, adaxial surface — Green, near RHS 137B. Mature foliage, abaxial surface — Green, near RHS 137B.
- *Venation.*—Parallel.
- *Venation color, adaxial surface.*—Green, near RHS 137B.
- *Venation color, abaxial surface.*—Green, near RHS 137B.
- *Petiole.*—No petioles present; leaves sessile.

Inflorescence:

- *Inflorescence arrangement.*—Axially placed raceme.
- *Natural flowering season.*—Autumn into winter.
- *Time to flower.*—Approximately 10 months.
- *Flowers per inflorescence.*—Average of 10; 7 open flowers and 3 buds.
- *Inflorescence height.*—Approximately 21.6 cm (measured from base of lowest flower to top of upper flower).

*Inflorescence diameter.*—Approximately 21.5 cm.

*Peduncle.*—Dimensions — Approximately 41.9 cm long and 0.6 cm wide. Aspect — Generally at a 15 degree angle to lateral branch axis. Strength — Moderately strong. Texture and luster — Glabrous and moderately glossy. Color — Yellow-green, RHS 144A.

Bud:

*Length.*—Average of 1.5 cm.

*Diameter.*—Average horizontal diameter is 1.5 cm; the vertical diameter is 2.1 cm.

*Shape.*—Cubic, with a deltoid apex which is pointed downward.

*Pubescence, texture and luster.*—Glabrous, smooth and matte.

*Color.*—Greyed-purple, in between near RHS 85B and N187B; the apex is tinged violet, RHS 83B.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 11.8 cm.

*Diameter.*—Approximately 11.2 cm.

*Depth.*—Approximately 4.5 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.5 cm. Width — Approximately 5.0 cm. Shape — Broad ovate to near orbicular. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — White, near RHS N155A, and fading to violet towards the apex and margins, near RHS N88C. Color when opening, lower surface — White, near RHS N155A, and fading to violet towards the apex and margins, near RHS N88C. Color when fully opened, upper surface — White, near RHS N155C, and fading to violet towards the apex and margins, near RHS N88D. Color when fully opened, lower surface — White, near RHS N155A, and fading to violet towards the apex and margins, near RHS N88D. Fading, upper surface — Not fading. Fading, lower surface — Not fading. Venation — Densely reticulate. Venation color, fully opened, upper surface — Violet, near RHS N88A to N88B. Venation color, fully opened, lower surface — Violet, near RHS N88A to N88B.

*Labellum.*—Shape — Three-lobed, lateral lobes are ovate and involute; central lobe is oblong and strongly revolute. Length — Central lobe — Approximately 2.4 cm. Lateral lobes — Approximately 1.0 cm. Width — Central lobe — Approximately 1.2 cm. Lateral lobes — Approximately 0.7 cm. Apex, central lobe — Straight to irregular. Apex, lateral lobes — Obtuse. Base, central and lateral lobes — Cuneate. Margin, central lobe — Irregular; slightly undulated. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Violet-blue, near RHS N92D. Lateral lobes — Purple, near RHS 77A, and purple-violet, near RHS N82A; base tinged yellow, near 13A. Color when opening, lower surface — Central lobe — Violet-blue, near RHS N92D, and fading to violet towards the base, near RHS N87C. Lateral lobes — Violet, near RHS N87D. Color when fully opened, upper surface — Central lobe — Violet-blue, near RHS N92D, and fading to violet, near RHS N88A, and violet-blue, near RHS 90A, towards the base. Lateral lobes — Purple, near RHS 77A, and purple-violet, near RHS N82A; base tinged yellow, near 13A. Color when fully opened, lower surface — Central lobe — Violet-blue, near RHS N89A, and fading to violet towards the base, near RHS N88C to N88D. Lateral lobes — Violet, near RHS N88B, and fading lighter towards the apex, near RHS N88D. Fading, upper surface — Not fading. Fading, lower surface — Not fading. Venation — No veins visible. Venation color, fully opened, upper surface — Central lobe — No veins visible. Lateral lobes — No veins visible. Venation color, fully opened, lower surface — Central lobe — No veins visible. Lateral lobes — No veins visible.

*Callosities.*—Dimensions — 1.9 cm long and 0.7 cm wide, on average. Color — Violet-blue, near RHS N89A, and fading to violet towards the base, near RHS 85C.

*Spurs.*—Quantity — Average of 1. Length — Approximately 1.0 cm. Diameter — Approximately 0.4 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Violet, near RHS 85D, and striped darker, near RHS 85A.

*Sepals.*—Quantity — Average of 3 unfused sepals. Arrangement — One dorsal sepal and two lateral sepals. Length — Dorsal sepal — Approximately 5.8 cm. Lateral sepals — Approximately 6.5 cm. Width — Dorsal sepal — Approximately 5.0 cm. Lateral sepals — Approximately 6.2 cm. Shape — Dorsal sepal — Broad ovate to near broad oblong. Lateral sepals — Broad ovate. Apex, dorsal and lateral sepals — Obtuse. Base, dorsal and lateral sepals — Cuneate. Margin, dorsal and lateral sepals — Entire; all sepals are slightly coarsely undulated. Pubescence, texture and luster — Glabrous, velvety, and matte on both the upper and lower sepal surfaces. Color when opening, upper surface — Dorsal sepal — Violet, near RHS N85D, and fading darker towards the apex and margins, near RHS N88C. Lateral sepals — Violet, near RHS N85D, and fading darker towards the apex and margins, near RHS N88C. Color when opening, lower surface — Dorsal sepal — Violet, near RHS N88D yet lighter, and fading darker towards the apex and margins, near RHS N88C. Lateral sepals — Violet, near RHS N88D yet lighter, and fading darker towards the apex and margins, near RHS N88C. Color when fully opened, upper surface — Dorsal sepal — White, near RHS NN155C, and fading to violet towards the margins and the apex, near RHS N88C to N88D. Lateral sepals — White, near RHS NN155D, and fading to violet towards the margins and the apex, near RHS N88C to N88D. Color when fully opened, lower surface — Dorsal sepal — White, near RHS NN155C, and fading to violet towards the margins and the apex, near RHS N88C to N88D. Lateral sepals — White, near RHS NN155C, and fading to violet towards the margins and the apex, near RHS N88C to N88D. Fading, upper surface — The color of all sepals does not fade. Fading, lower surface — The color of all sepals does not fade. Venation — Densely reticulate. Venation color, fully opened, upper surface — Violet, near RHS N88A to N88B. Venation color, fully opened, lower surface — Violet, near RHS N88B.

*Pedicels.*—Length — Approximately 6.3 cm. Diameter — Approximately 0.5 cm. Angle — Approximately 80 degree angle to peduncle axis. Strength — Moderate. Texture — Glabrous, axially angled with 5 "ribs", axially twisted (due to resupination). Luster — Glossy. Color — Purple, near RHS 85A, and fading to purple-violet towards the proximal end, near RHS N81B.

*Bract.*—Quantity — One bract present at the base of each pedicel. Shape — Broad ovate; folded around the base of each pedicel. Dimensions — Average of 1.2 cm long and 1.1 cm wide. Apex — Broad acute. Base — Broad cuneate. Margins — Entire. Color, both surfaces — Yellow-green, near RHS 144C.

Reproductive organs:

*Column.*—Length — Approximately 0.6 cm. Diameter — Approximately 0.8 cm. Color — Purple, RHS 76B and 76C.

*Ovary.*—Position — Inferior. Diameter — Approximately 1.1 cm. Color — Yellow-green, RHS 150D.

*Pollinia color.*—Yellow-orange, RHS 15A.

Seed and fruit: No fruit and seed production has been detected to date.

COMPARISON WITH THE PARENT PLANTS

Plants of the new cultivar 'SPCDW1508' differ from the unnamed *Vanda* seed parent (not patented) by the characteristics described in Chart 1.

CHART 1

| Characteristic | 'SPCDW1508' | Unnamed seed parent |
|---|---|---|
| Color pattern on the petals and sepals. | Dense irregular tessellation pattern; pattern is generally colored violet. | Light irregular tessellation pattern; pattern is generally colored violet-blue. |
| Inflorescence. | Racemes are longer than those of the seed parent, with fewer flowers. | Racemes are shorter than those of 'SPCDW1508', with more flowers. |

CHART 1-continued

| Characteristic | 'SPCDW1508' | Unnamed seed parent |
|---|---|---|
| Flower size. | Larger flowers than seed parent. | Smaller flowers than 'SPCDW1508'. |
| Plant vigor. | More vigorous and faster growing than the seed parent. | Less vigorous and slower growing than 'SPCDW1508'. |
| Length of foliage. | Leaves are longer than those of seed parent. | Leaves are shorter than those of 'SPCDW1508'. |

Plants of the new cultivar 'SPCDW1508' differ from the unnamed *Vanda* pollen parent (not patented) by the characteristics described in Chart 2.

CHART 2

| Characteristic | 'SPCDW1508' | Unnamed pollen parent |
|---|---|---|
| Color pattern on the petals and sepals. | More prominent tessellation pattern; pattern is generally colored violet. | Light tessellation pattern; pattern is generally colored violet-blue. |
| Inflorescence. | Racemes are longer than those of the pollen parent, with more flowers. | Racemes are shorter than those of 'SPCDW1508', with fewer flowers. |
| Plant vigor. | More vigorous and faster growing than the pollen parent. | Less vigorous and slower growing than 'SPCDW1508'. |

COMPARISON WITH THE MOST SIMILAR *VANDA* CULTIVAR KNOWN TO THE INVENTOR

Plants of the new cultivar 'SPCDW1508' are most similar to the cultivar, *Vanda* 'SPCDW1110' (U.S. Plant Pat. No. 24,988). A comparison of 'SPCDW1508' with *Vanda* 'SPCDW1110' is described in Chart 3.

CHART 3

| Characteristic | 'SPCDW1508' | 'SPCDW1110' |
|---|---|---|
| Petal and sepal aspect. | Somewhat twisted or spiraled in a propeller-like fashion. | Flat. |
| Flower Petal Arrangement | Higher degree of sepal overlap compared to 'SPCDW1110'. | Lesser degree of sepal overlap compared to 'SPCDW1508'. |
| Dorsal sepal cross-section. | Much less incurved than 'SPCDW1110'. | Much more incurved than 'SPCDW1508'. |
| Dorsal sepal apex. | Less rounded than 'SPCDW1110'. | More rounded than 'SPCDW1508'. |
| Color pattern on the petals and sepals. | Less prominent tessellation pattern; pattern is generally colored violet. | More prominent tessellation pattern; pattern is generally colored violet-blue. |
| Labellum width. | Wider than 'SPCDW1110'. | Narrower than 'SPCDW1508'. |
| Labellum, lateral lobe dimensions. | Larger than 'SPCDW1110'. | Smaller than 'SPCDW1508'. |

That which is claimed is:

1. A new and distinct variety of *Vanda* plant named 'SPCDW1508', substantially as described and illustrated herein.

* * * * *